United States Patent
Desos et al.

(10) Patent No.: US 7,262,190 B2
(45) Date of Patent: Aug. 28, 2007

(54) BENZOTHIAZINE AND BENZOTHIADIAZINE COMPOUNDS

(75) Inventors: Patrice Desos, Bois-Colombes (FR); Alexis Cordi, Suresnes (FR); Pierre Lestage, La Celle-Saint-Cloud (FR); Laurence Danober, Montesson (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/297,260

(22) Filed: Dec. 8, 2005

(65) Prior Publication Data

US 2006/0128697 A1    Jun. 15, 2006

(30) Foreign Application Priority Data

Dec. 10, 2004   (FR) .................................. 04 13170

(51) Int. Cl.
- *C07D 513/04* (2006.01)
- *C07D 285/26* (2006.01)
- *A61K 31/542* (2006.01)
- *A61P 25/24* (2006.01)

(52) U.S. Cl. .................. 514/222.8; 544/9; 544/12; 544/49; 514/215; 514/214.02; 514/223.2; 514/224.5; 540/578

(58) Field of Classification Search ............. 544/9, 544/12, 49; 514/214.02, 223.2, 224.5; 540/578

See application file for complete search history.

(56) References Cited

OTHER PUBLICATIONS

Alt et al. Current Pharmaceutical Design, 2005, 11, 1511-1527.*
Black et al Psychopharmacology (2005) 179: 154-163.*
* cited by examiner

*Primary Examiner*—Kahsay Habte
(74) *Attorney, Agent, or Firm*—Hueschen and Sage

(57) ABSTRACT

The invention relates to compounds of formula (I):

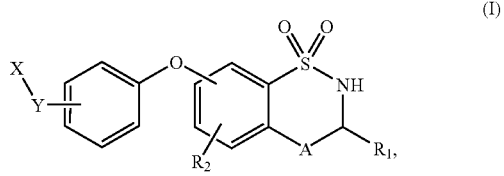

wherein:
$R_1$ represents hydrogen, alkyl or cycloalkyl,
$R_2$ represents hydrogen, halogen or hydroxy,
A represents $CR_3R_4$ or $NR_3$ wherein $R_3$ and $R_4$ are as defined in the description,
Y represents an alkylene chain as described in the description,
X represents $NR_5R_6$, $S(O)_nR_7$, $OR_8$, $C(O)R_9$, amidino or a heterocycle,
their isomers, and addition salts thereof;
and medicinal products containing the same which are useful in the prevention or treatment of diseases associated with AMPA flux.

8 Claims, No Drawings

BENZOTHIAZINE AND BENZOTHIADIAZINE COMPOUNDS

FIELD OF THE INVENTION

The present invention relates to new benzothiazine and benzothiadiazine compounds, to a process for their preparation and to pharmaceutical compositions containing them.

BACKGROUND OF THE INVENTION

It has now been recognised that the excitatory amino acids, very especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral Reviews, 1992, 16, 13-24; Progress in Neurobiology, 1992, 39, 517-545).

In addition, innumerable works have in recent years demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor appears to be involved to the greatest extent in the phenomena of physiological neuronal excitability and, especially, in those phenomena involved in memorisation processes. For example, it has been shown that learning is associated with an increase in the binding of AMPA to its receptor in the hippocampus, one of the areas of the brain essential to processes of memory and cognition. Likewise, nootropic agents such as aniracetam have very recently been described as modulating the AMPA receptors of neuronal cells in a positive manner (Journal of Neurochemistry, 1992, 58, 1199-1204).

DESCRIPTION OF THE PRIOR ART

In the literature, compounds having a benzamide structure have been described as possessing this same mechanism of action and as improving memory performance (Synapse, 1993, 15, 326-329). Compound BA 74, in particular, is the most active of those new pharmacological agents.

Finally, the patent specification EP 692 484 describes a benzothiadiazine compound having facilitating activity on the AMPA current, and the patent application WO 99/42456 describes, inter alia, certain benzothiadiazine compounds as modulators of AMPA receptors.

The benzothiazine and benzothiadiazine compounds to which the present invention relates, besides being new, surprisingly exhibit pharmacological activity on the AMPA current that is markedly superior to the activity of the compounds of similar structure described in the prior art. They are useful as AMPA modulators for the treatment or prevention of disorders of memory and cognition that are associated with age, with syndromes of anxiety or depression, with progressive neurodegenerative diseases, with Alzheimer's disease, with Pick's disease, with Huntington's chorea, with schizophrenia, with the sequelae of acute neurodegenerative diseases, with the sequelae of ischaemia and with the sequelae of epilepsy.

DETAILED DESCRIPTION OF THE INVENTION

More specifically, the present invention relates to compounds of formula (I):

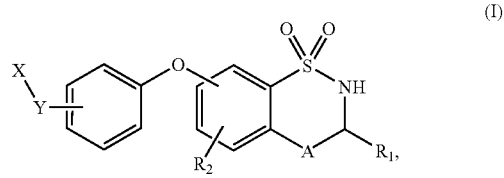

wherein:

$R_1$ represents a hydrogen atom, a linear or branched ($C_1$-$C_6$)alkyl group or a ($C_3$-$C_7$)cycloalkyl group, $R_2$ represents a hydrogen atom, a halogen atom or a hydroxy group, A represents a $CR_3R_4$ group or an $NR_3$ group wherein $R_3$ represents a hydrogen atom or a linear or branched ($C_1$-$C_6$)alkyl group, and $R_4$ represents a hydrogen atom or a halogen atom, or A represents a nitrogen atom and, together with the adjacent —$CHR_1$— group, forms the ring

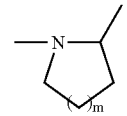

wherein m represents 1, 2 or 3,

Y represents a ($C_2$-$C_6$)alkylene chain optionally substituted by one or more identical or different substituents selected from linear or branched ($C_1$-$C_6$)alkyl groups and halogen atoms and wherein one of the —$CH_2$— groups may be replaced by a group

wherein p is 1, 2, 3 or 4,
or Y represents a group

as defined hereinbefore,

X represents an $NR_5R_6$, $S(O)_nR_7$, $OR_8$, $C(O)R_9$, amidino (optionally substituted by one or two identical or different groups selected from linear or branched ($C_1$-$C_6$)alkyl, hydroxy, linear or branched ($C_1$-$C_6$)alkoxy and

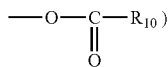

or heterocyclic group wherein:
- $R_5$ represents a hydrogen atom or a linear or branched $(C_1-C_6)$alkyl, $S(O)_tR_{11}$, $COR_{12}$ or $P(O)OR_{13}OR_{14}$ group,
- $R_6$ represents a hydrogen atom or a linear or branched $(C_1-C_6)$alkyl group,
- or $R_5$ and $R_6$, together with the nitrogen atom carrying them, form a heterocyclic group,
- $R_8$ represents a linear or branched $(C_1-C_6)$alkyl group or a $C(O)R_{15}$ group,
- $R_9$ represents a hydroxy group, a linear or branched $(C_1-C_6)$alkoxy group, or an amino group (optionally substituted by one or two identical or different linear or branched $(C_1-C_6)$alkyl groups),
- $R_7$, $R_{10}$, $R_{11}$, $R_{12}$, $R_{13}$, $R_{14}$ and $R_{15}$, which may be the same or different, each represent a hydrogen atom; a linear or branched $(C_1-C_6)$alkyl group optionally substituted by one or more halogen atoms; an aryl-$(C_1-C_6)$alkyl group in which the alkyl moiety is linear or branched; or an aryl group,
- n and t, which may be the same or different, each represent 0, 1 or 2, to their enantiomers and diastereoisomers, and also to addition salts thereof with a pharmaceutically acceptable acid or base, it being understood that:
- a heterocyclic group means a monocyclic or bicyclic, aromatic or non-aromatic group containing from one to four identical or different hetero atoms selected from nitrogen, oxygen and sulphur, optionally substituted by one or more identical or different groups selected from halogen, linear or branched $(C_1-C_6)$alkyl, linear or branched $(C_1-C_6)$alkoxy, linear or branched $(C_1-C_6)$polyhaloalkyl, linear or branched $(C_1-C_6)$alkoxy-carbonyl, oxo, thioxo, carboxy, linear or branched $(C_1-C_6)$acyl, linear or branched $(C_1-C_6)$polyhaloalkoxy, hydroxy, cyano, nitro, amino (optionally substituted by one or more linear or branched $(C_1-C_6)$alkyl groups), aminosulphonyl (optionally substituted by one or more linear or branched $(C_1-C_6)$alkyl groups) and $(C_1-C_6)$alkylsulphonylamino,
- an aryl group means a monocyclic aromatic group or a bicyclic group in which at least one of the rings is aromatic, containing from 5 to 10 carbon atoms, optionally substituted by one or more identical or different groups selected from halogen, linear or branched $(C_1-C_6)$alkyl (optionally substituted by one or more hydroxy groups), linear or branched $(C_1-C_6)$alkoxy, linear or branched $(C_1-C_6)$polyhaloalkyl, linear or branched $(C_1-C_6)$alkoxy-carbonyl, oxo, thioxo, linear or branched $(C_1-C_6)$alkylthio, carboxy, linear or branched $(C_1-C_6)$acyl, linear or branched $(C_1-C_6)$polyhaloalkoxy, hydroxy, cyano, nitro, amino (optionally substituted by one or more linear or branched $(C_1-C_6)$alkyl or linear or branched $(C_1-C_6)$acyl groups), aminocarbonyl (optionally substituted by one or more linear or branched $(C_1-C_6)$alkyl groups), aminosulphonyl (optionally substituted by one or more linear or branched $(C_1-C_6)$alkyl groups), mono- or di-$((C_1-C_6)$alkylsulphonyl)amino, mono- or di-(trifluoromethylsulphonyl)amino, $PO(OR_a)(OR_b)$ (wherein $R_a$ and $R_b$, which may be the same or different, each represent a hydrogen atom or a linear or branched $(C_1-C_6)$alkyl group), benzyloxy and phenyl (optionally substituted by one or more identical or different groups selected from halogen, linear or branched $(C_1-C_6)$alkyl, linear or branched $(C_1-C_6)$polyhaloalkyl, hydroxy and linear or branched $(C_1-C_6)$alkoxy).

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

The invention relates more especially to compounds of formula (I) wherein A represents a nitrogen atom and, together with the adjacent —CHR$_1$— group, forms the ring

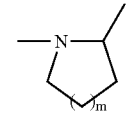

wherein m represents 1, 2 or 3, and more especially the ring

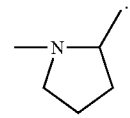

Preference is given to the $R_2$ group being a hydrogen atom.

Y preferably represents an unsubstituted or substituted alkylene chain containing 2 or 3 carbon atoms. Where present, substituents of the alkylene chain representing Y that are preferred are a fluorine atom or a methyl group.

Preference is given to the X group being an $NR_5R_6$ or $C(O)R_9$ group, more especially the group $NHSO_2R_{11}$ wherein $R_{11}$ preferably represents a linear or branched $(C_1-C_6)$alkyl group.

Even more especially, the invention relates to compounds of formula (I) which are:
- N-(2-{4-[(5,5-dioxido-2,3,3a,4-tetrahydro-1H-pyrrolo[2,1-c][1,2,4]benzothiadiazin-7-yl)-oxy]phenyl}ethyl)methanesulphonamide,
- 3-{4-[(5,5-dioxido-2,3,3a,4-tetrahydro-1H-pyrrolo[2,1-c][1,2,4]benzothiadiazin-yl)oxy]-phenyl}propanoic acid,
- 3-{4-[(5,5-dioxido-2,3,3a,4-tetrahydro-1H-pyrrolo[2,1-c][1,2,4]benzothiadiazin-7-yl)oxy]-phenyl}propanamide,
- 3-{4-[(5,5-dioxido-2,3,3a,4-tetrahydro-1H-pyrrolo[2,1-c][1,2,4]benzothiadiazin-7-yl)oxy]oxy]-phenyl}-N,N-dimethylpropanamide,
- N-(3-{4-[(5,5-dioxido-2,3,3a,4-tetrahydro-1H-pyrrolo[2,1-c][1,2,4]benzothiadiazin-7-yl)-oxy]phenyl}propyl)methanesulphonamide, N-(2-{4-[(5,5-dioxido-2,3,3a,4-tetrahydro-1H-pyrrolo[2,1-c][1,2,4]benzothiadiazin-7yl)-oxy]phenyl}-2-fluoropropyl)-2-propanesulphonamide, N-(2-{4-[(5,5-dioxido-2,3,3a,4-tetrahydro-1H-pyrrolo[2,1-c][1,2,4]benzothiadiazin-7-yl)-oxy]phenyl}-2-fluoropropyl)methanesulphonamide, N-(2-{4-[(5,5-dioxido-2,3,3a,4-tetrahydro-1H-pyrrolo[2,1-c][1,2,4]benzothiadiazin-7-yl)-oxy]phenyl}propyl)methanesulphonamide, N-(2-{4-[(5,5-dioxido-2,3,3a,4-tetrahydro-1H-pyrrolo[2,1-c][1,2,4]benzothiadiazin-7-yl)-oxy]phenyl}ethyl)-N,N-dimethylamine, N-(1-{4-[(5,5-dioxido-2,3,3a,4-tetrahydro-1H-pyrrolo[2,1-c][1,2,4]benzothiadiazin-7-yl)-oxy]phenyl}cyclopropyl)methanesulphonamide.

The invention relates also to a process for the preparation of compounds of formula (I), which process is characterised in that there is used as starting material the compound of formula (II):

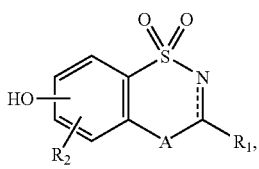
(II)

wherein A, $R_1$ and $R_2$ are as defined for formula (I) and the symbol ---- means that the bond is single or double, which is reacted, in the presence of copper(II) acetate, with a boronic acid compound of formula (III):

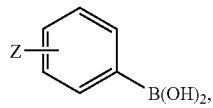
(III)

wherein Z represents a linear or branched $(C_1-C_6)$acyl group, a group —Y—X wherein X and Y are as defined for formula (I), or a group —Y—X' wherein Y is as defined for formula (I) and X' represents a cyano or carboxy group, to yield, directly or after reduction (when the symbol ---- represents a double bond) by a metal hydride and/or by optional conversion of the X' group or the acyl group, the compound of formula (I):

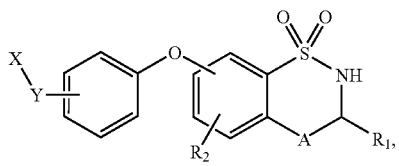
(I)

which compound of formula (I) is purified, if necessary, according to a conventional purification technique, is separated, where appropriate, into its isomers according to a conventional separation technique and is converted, if desired, into its addition salts with a pharmaceutically acceptable acid or base.

The compounds of formula (II) as defined hereinbefore are obtained by conventional reactions of organic chemistry and more especially by means of the process described in WO03053979.

The invention relates also to pharmaceutical compositions comprising, as active ingredient, a compound of formula (I) with one or more appropriate, inert, non-toxic excipients.

Among the pharmaceutical compositions according to the invention there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions etc.

The useful dosage can be varied according to the nature and severity of the disorder, the administration route and the age and weight of the patient and ranges from 1 to 500 mg per day in one or more administrations.

The Examples that follow illustrate the invention but do not limit it in any way.

The starting materials used are products that are known or that are prepared according to known operating procedures.

The structures of the compounds described in the Examples were determined according to the usual spectrophotometric techniques (infrared, NMR, mass spectrometry, . . . ).

EXAMPLE 1

N-(2-{4-[(5,5-Dioxido-2,3,3a,4-tetrahydro-1H-pyrrolo[2,1-c][1,2,4]benzo-thiadiazin-7-yl)oxy]phenyl}ethyl)methanesulphonamide 25 ml of $CH_2Cl_2$, 240 µl (2.96 mmol) of pyridine, 238 mg (0.99 mmol) of 2,3,3a,4-tetrahydro-1H-pyrrolo[2,1-c][1,2,4]benzothiadiazin-7-ol 5,5-dioxide, 2.5 g of 4 Å molecular sieve, 340 mg (1.48 mmol) of 4-{2-[(methylsulphonyl)amino]ethyl}phenylboronic acid and 270 mg (1.48 mmol) of $Cu(OAc)_2$ are introduced into a 100 ml Erlenmeyer flask. The suspension is stirred vigorously at ambient temperature, the Erlenmeyer flask being left open to the air. After 4 hours 30 minutes, the reaction mixture is diluted with an additional 50 ml of $CH_2Cl_2$ and the suspension is filtered. The filtrate is evaporated to dryness and the residue is purified by successively chromatographing twice on a silica column, eluting with $CH_2Cl_2$/acetone (96/4) in the first chromatographic procedure and with $CH_2Cl_2$/AcOEt (70/30) in the second. The colourless oil obtained is crystallised by triturating in a mixture of $Et_2O$ and a few drops of isopropanol to yield, after filtration, the title compound in the form of a white powder.

Melting point: 99-102° C.

Elemental microanalysis:

|  | C | H | N | S |
|---|---|---|---|---|
| theoretical % | 52.16 | 5.30 | 9.60 | 14.66 |
| experimental % | 52.57 | 5.42 | 9.67 | 14.92 |

EXAMPLE 2

3-{4-[(5,5-Dioxido-2,3,3a,4-tetrahydro-1H-pyrrolo[2,1-c][1,2,4]benzothiadiazin-7-yl)oxy]phenyl}propanoic acid

Step A: Methyl 3-{4-[(5,5-dioxido-2,3-dihydro-1H-pyrrolo[2,1-c][1,2,4]benzothiadiazin-7-yl)oxy]phenyl}propanoate The title compound is obtained by reacting 2,3-dihydro-1H-pyrrolo[2,1-c][1,2,4]benzo-thiadiazin-7-ol 5,5-dioxide with 4-(3-methoxy-3-oxopropyl)phenylboronic acid according to the procedure of Example 1, although extending the reaction time to 48 hours. Purification is carried out by chromatography on a silica column, eluting with a mixture of $CH_2Cl_2$/acetone 95/5.

Melting point: 138-140° C.

Elemental microanalysis:

|  | C | H | N | S |
|---|---|---|---|---|
| theoretical % | 59.99 | 5.03 | 7.00 | 8.01 |
| experimental % | 59.96 | 5.12 | 6.90 | 7.51 |

Step B: 3-{4-[(5,5-Dioxido-2,3-dihydro-1H-pyrrolo[2,1-c][1,2,4]benzothiadiazin-7-yl)oxy]phenyl}propanoic acid A suspension of 580 mg (1.45 mmol) of the compound obtained in Step A is stirred at reflux in 9 ml of 1N HCl for 5 hours. The reaction mixture is then diluted with water and the suspension is filtered to yield the title compound in the form of a white solid.

Melting point: 216-222° C.

Elemental microanalysis:

|  | C | H | N | S |
|---|---|---|---|---|
| theoretical % | 59.06 | 4.70 | 7.25 | 8.30 |
| experimental % | 59.34 | 4.87 | 7.27 | 8.35 |

Step C: 3-{4-[(5,5-Dioxido-2,3,3a,4-tetrahydro-1H-pyrrolo[2,1-c][1,2,4]-benzothiadiazin-7-yl)oxy]phenyl}propanoic acid 62 mg (1.63 mmol) of $NaBH_4$ are added to a suspension of 210 mg (0.54 mmol) of the compound of the previous Step in 6 ml of ethanol. After stirring for 2 hours at ambient temperature, the reaction solution is cooled in an ice bath and acidified by the addition of 1N HCl. The gummy suspension is extracted with $CH_2Cl_2$; the organic phase is then washed with saturated aqueous NaCl solution, dried over $MgSO_4$ and evaporated. The residue is triturated in $Et_2O$ and the white solid formed is filtered off to yield the title compound.

Melting point: 178-183° C.

Elemental microanalysis:

|  | C | H | N | S |
|---|---|---|---|---|
| theoretical % | 58.75 | 5.19 | 7.21 | 8.25 |
| experimental % | 58.73 | 5.24 | 7.11 | 8.41 |

EXAMPLE 3

3-{4-[(5,5-Dioxido-2,3,3a,4-tetrahydro-1H-pyrrolo[2,1-c][1,2,4]benzo-thiadiazin-7-yl)oxy]phenyl}propanamide

Step A: 3-{4-[(5,5-Dioxido-2,3-dihydro-1H-pyrrolo[2,1-c][1,2,4]benzothiadiazin-7-yl)-oxy]phenyl}propanamide 415 mg (1.30 mmol) of TBTU are added to a suspension (500 mg, 1.30 mmol) of the compound obtained in Step B of Example 2 in 25 ml of $CH_2Cl_2$. The suspension is stirred at ambient temperature for 10 minutes and 293 µl (1.68 mmol) of diisopropylethylamine are added. The reaction mixture becomes a solution and stirring is continued for 10 minutes. The solution is then saturated with ammonia gas and stirring is continued for 30 minutes. Thin-layer chromatography (AcOEt) indicates that all the starting material has disappeared. The reaction mixture is then acidified by adding 1N HCl; the organic phase is decanted off, washed (water and then saturated NaCl solution), dried ($MgSO_4$) and evaporated. The residue is triturated in $Et_2O$ and the white solid formed is filtered off to yield the title product.

Melting point: 178-183° C.

Step B: 3-{4-[(5,5-Dioxido-2,3,3a,4-tetrahydro-1H-pyrrolo[2,1-c][1,2,4]benzo-thiadiazin-7-yl)oxy]phenyl}propanamide The procedure is in accordance with Step C of Example 2, starting from the compound obtained in Step A.

Melting point: 195-198° C.

Elemental microanalysis:

|  | C | H | N | S |
|---|---|---|---|---|
| theoretical % | 58.9 | 5.46 | 10.85 | 8.28 |
| experimental % | 58.55 | 5.47 | 10.40 | 8.24 |

EXAMPLE 4

3-{4-[(5,5-Dioxido-2,3,3a,4-tetrahydro-1H-pyrrolo[2,1-c][1,2,4]benzo-thiadiazin-7-yl)oxy]phenyl}-N,N-dimethylpropanamide

Step A: 3-{4-[(5,5-Dioxido-2,3-dihydro-1H-pyrrolo[2,1-c][1,2,4]benzothiadiazin-7-yl)oxy]phenyl}-N,N-dimethylpropanamide The procedure is as in Step A of Example 3 but replacing the ammonia gas by 2M dimethylamine in THF. Purification is carried out by chromatography on a silica column, eluting with a mixture of $CH_2Cl_2$/MeOH 98/2.

Melting point: 77-80° C.

Step B: 3-{4-[(5,5-Dioxido-2,3,3a,4-tetrahydro-1H-pyrrolo[2,1-c][1,2,4]benzo-thiadiazin-7-yl)oxy]phenyl}-N,N-dimethylpropanamide The procedure is in accordance with Step C of Example 2, starting from the compound obtained in Step A. Purification is carried out by chromatography on a silica column, eluting with a mixture of $CH_2Cl_2$/acetone 90/10.

Melting point: 189-192° C.

Elemental microanalysis:

|  | C | H | N | S |
|---|---|---|---|---|
| theoretical % | 60.70 | 6.06 | 10.11 | 7.72 |
| experimental % | 61.24 | 6.37 | 10.16 | 7.68 |

EXAMPLE 5

N-(3-{4-[(5,5-Dioxido-2,3,3a,4-tetrahydro-1H-pyrrolo[2,1-c][1,2,4]-benzothiadiazin-7-yl)oxy]phenyl}propyl)methanesulphonamide Step A: (3-{4-[(5,5-Dioxido-2,3,3a,4-tetrahydro-1H-pyrrolo[2,1-c][1,2,4]benzo-thiadiazin-7-yl)oxy]phenyl}propyl)amine 192 mg (5.06 mmol) of $LiAlH_4$ are added, in small portions, to a suspension (390 mg, 1.01 mmol) of the compound obtained in Step A of Example 3 in 20 ml of THF and the reaction mixture is stirred at reflux for 1 hour 30 minutes. The reaction mixture is cooled in an ice bath and is treated by the dropwise addition of aqueous $NH_4Cl$ solution. The aluminium salts are filtered off and rinsed with THF and then with acetone, and the filtrate is concentrated. The latter is diluted with $CH_2Cl_2$ and the amine of the title is extracted with 1N HCl. The acidic aqueous phase is washed with $CH_2Cl_2$, made alkaline with 10% $NaHCO_3$ solution and extracted three times with AcOEt. The organic phases are collected, dried over $MgSO_4$ and evaporated. The residue is triturated in $Et_2O$ and the white solid formed is filtered off to yield the title compound.

Melting point: 126-131° C.

Step B: N-(3-{4-[(5,5-Dioxido-2,3,3a,4-tetrahydro-1H-pyrrolo[2,1-c][1,2,4]benzo-thiadiazin-7-yl)oxy]phenyl}propyl)methanesulphonamide To a solution, at 0° C., of the compound obtained in Step A (106 mg, 0.28 mmol) in 2 ml of $CH_2Cl_2$, cooled in an ice bath, there are added 59 μL (0.43 mmol) of triethylamine and then, dropwise, 74 mg (0.43 mmol) of methanesulphonic acid dissolved in 2 ml of $CH_2Cl_2$. The reaction solution is stirred for 2 hours while being allowed to return to ambient temperature. The organic phase is washed with 1N HCl and then with saturated aqueous NaCl solution and is dried over $MgSO_4$. After evaporation, the title compound is purified by chromatography on a silica column, eluting with a mixture of $CH_2Cl_2$/acetone 95/5.

Melting point: 65-69° C.

Elemental microanalysis:

|  | C | H | N | S |
|---|---|---|---|---|
| theoretical % | 53.20 | 5.58 | 9.31 | 14.20 |
| experimental % | 53.24 | 5.64 | 9.12 | 14.40 |

EXAMPLE 6

N-((2S)-2-{4-[(5,5-Dioxido-2,3,3a,4-tetrahydro-1H-pyrrolo[2,1-c][1,2,4]-benzothiadiazin-7-yl)oxy]phenyl}-2-fluoropropyl)propane-2-sulphonamide The title compound is obtained by reacting 2,3,3a,4-tetrahydro-1H-pyrrolo[2,1-c][1,2,4]-benzothiadiazin-7-ol 5,5-dioxide with 4-{1-fluoro-2-[(isopropylsulphonyl)amino]-1-methyl-ethyl}phenylboronic acid according to the procedure of Example 1, although extending the reaction time to 16 hours. Purification is carried out by successively chromatographing twice on a silica column, eluting with a mixture of $CH_2Cl_2$/MeOH 98/2 in the first chromatographic procedure and with a mixture of cyclohexane/ethyl acetate 70/30 in the second.

Melting point: 90° C.

Elemental microanalysis:

|  | C | H | N | S |
|---|---|---|---|---|
| theoretical % | 53.10 | 5.67 | 8.44 | 12.89 |
| experimental % | 53.81 | 5.76 | 8.21 | 12.72 |

EXAMPLE 7

N-(2-{4-[(5,5-Dioxido-2,3,3a,4-tetrahydro-1H-pyrrolo[2,1-c][1,2,4]benzo-thiadiazin-7-yl)oxy]phenyl}-2-fluoropropyl)methanesulphonamide Step A: 1-{4-[(5,5-Dioxido-2,3,3a,4-tetrahydro-1H-pyrrolo[2,1-c][1,2,4]benzothiadiazin-7-yl)oxy]phenyl}ethanone The title compound is obtained by reacting 2,3,3a,4-tetrahydro-1H-pyrrolo[2,1-c][1,2,4]-benzothiadiazin-7-ol 5,5-dioxide with 4-acetylphenylboronic acid according to the procedure of Example 1, although extending the reaction time to 16 hours. Purification is carried out by chromatography on a silica column, eluting with a mixture of $CH_2Cl_2$/acetone 98/2.

Melting point: 150-152° C.

Step B: 1-Amino-2-{4-[(5,5-dioxido-2,3,3a,4-tetrahydro-1H-pyrrolo[2,1-c][1,2,4]-benzothiadiazin-7-yl)oxy]phenyl}propan-2-ol To a solution containing 1.0 g (2.79 mmol) of the compound obtained in Step A, 23 mg (0.09 mmol) of 18-crown-6 ether and 18.5 mg (0.28 mmol) of KCN in 25 ml of THF there are added, dropwise, 840 μl (6.26 mmol) of TMSCN. The reaction solution is stirred for 3 hours at ambient temperature and then 424 mg (11.2 mmol) of $LiAlH_4$ are added in small portions. After 1 hour 30 minutes, the excess hydride is hydrolysed by dropwise addition of saturated aqueous NaCl solution. The reaction mixture is filtered, the solid is rinsed several times with THF and the filtrate is evaporated to yield a white meringue corresponding to the title compound.

Melting point: 76-78° C.

Step C: N-(2-{4-[(5,5-Dioxido-2,3,3a,4-tetrahydro-1H-pyrrolo[2,1-c][1,2,4]benzo-thiadiazin-7-yl)oxy]phenyl}-2-hydroxypropyl)methanesulphonamide To a solution of the compound obtained in Step B (640 mg, 1.64 mmol) in 25 ml of $CH_2Cl_2$, cooled in an ice bath, there are added 354 μL (2.53 mmol) of triethylamine and then, dropwise, 441 mg (2.53 mmol) of methanesulphonic anhydride dissolved in 10 ml of $CH_2Cl_2$. The reaction solution is stirred for 2 hours while being allowed to return to ambient temperature. The organic phase is washed with 1N HCl and then saturated NaCl solution and is dried over $MgSO_4$. After evaporation, the residue is purified by chromatography on a silica column, eluting with a mixture of $CH_2Cl_2$/MeOH 96/4.

Melting point: 90-92° C.

Step D: N-(2-{4-[(5,5-Dioxido-2,3,3a,4-tetrahydro-1H-pyrrolo[2,1-c][1,2,4]benzo-thiadiazin-7-yl)oxy]phenyl}-2-fluoropropyl)methanesulphonamide To a solution of the compound obtained in Step C (230 mg, 0.49 mmol) in 15 ml of $CH_2Cl_2$, cooled in an ice bath, there are added, dropwise, 133 μL (0.99 mmol) of DAST. The reaction solution is stirred for 2 hours, while being allowed to return to ambient temperature. The organic phase is washed with $H_2O$ and then with saturated NaCl solution and is dried over $MgSO_4$. After evaporation, the residue is purified by chromatography on a silica column, eluting with a mixture of $CH_2Cl_2$/MeOH 99/1.

Melting point: 84-86° C.
Elemental microanalysis:

|  | C | H | N | S |
|---|---|---|---|---|
| theoretical % | 51.16 | 5.15 | 8.95 | 13.66 |
| experimental % | 51.34 | 5.48 | 8.91 | 14.16 |

EXAMPLE 8

N-(2-{4-[(5,5-Dioxido-2,3,3a,4-tetrahydro-1H-pyrrolo[2,1-c][1,2,4]benzo-thiadiazin-7-yl)oxy]phenyl}propyl)methanesulphonamide Step A: 2-{4-[(5,5-Dioxido-2,3,3a,4-tetrahydro-1H-pyrrolo[2,1-c][1,2,4]benzothiadiazin-7-yl)oxy]phenyl}propanenitrile 840 mg (4.30 mmol) of tosylmethylisonitrile are added to a solution of the compound of Step A of Example 7 (700 mg, 1.95 mmol) in 25 ml of 1,2-dimethoxyethane. The reaction solution is cooled to −25° C., and 6 ml (6 mmol) of 1M tBuOK in THF are added dropwise. The reaction mixture is stirred for 30 minutes at −25° C. and is then allowed to return to ambient temperature over 1 hour. After adding 1N HCl, the reaction mixture is extracted with AcOEt; the organic phases are collected, washed with saturated NaCl solution and dried ($MgSO_4$). After evaporation, the residue is purified by chromatography on a silica column, eluting with a mixture of $CH_2Cl_2$MeOH 99/1 to yield a white meringue corresponding to the title compound.

Step B: (2-{4-[(5,5-Dioxido-2,3,3a,4-tetrahydro-1H-pyrrolo[2,1-c][1,2,4]benzothiadiazin-7-yl)oxy]phenyl}propyl)amine 200 mg (5.25 mmol) of $LiAlH_4$, in small portions, are added to a solution containing 485 mg (1.31 mmol) of the compound of Step A above in 15 ml of THF. After reacting for 3 hours, the excess hydride is hydrolysed by dropwise addition of saturated aqueous NaCl solution. The reaction mixture is filtered, the solid is rinsed several times with THF and the filtrate is evaporated to yield a white meringue corresponding to the title compound.

Step C: N-(2-{4-[(5,5-Dioxido-2,3,3a,4-tetrahydro-1H-pyrrolo[2,1-c][1,2,4]benzo-thiadiazin-7-yl)oxy]phenyl}propyl)methanesulphonamide To a solution of the compound obtained in Step B (394 mg, 1.06 mmol) in 20 ml of $CH_2Cl_2$, cooled in an ice bath, there are added 441 μL (3.17 mmol) of triethylamine and then, dropwise, 404 mg (2.32 mmol) of methanesulphonic anhydride dissolved in 5 ml of $CH_2Cl_2$. The reaction solution is stirred for 2 hours while being allowed to return to ambient temperature. The organic phase is washed with 1N HCl and then saturated NaCl solution and is dried over $MgSO_4$. After evaporation, the residue is purified by chromatography on a silica column, eluting with a mixture of $CH_2Cl_2$/MeOH 99/1.

Melting point: 83-85° C.
Elemental microanalysis:

|  | C | H | N | S |
|---|---|---|---|---|
| theoretical % | 53.2 | 5.58 | 9.31 | 14.2 |
| experimental % | 53.53 | 5.67 | 9.05 | 14.26 |

EXAMPLE 9

(2-{4-[(5,5-Dioxido-2,3,3a,4-tetrahydro-1H-pyrrolo[2,1-c][1,2,4]benzothiadiazin-7-yl)oxy]phenyl}ethyl)dimethylamine Step A: Methyl {4-[(5,5-dioxido-2,3,3a,4-tetrahydro-1H-pyrrolo[2, 1-c][1,2,4]benzo-thiadiazin-7-yl)oxy]phenyl}acetate The title compound is obtained by reacting 2,3,3a,4-tetrahydro-1H-pyrrolo[2,1-c][1,2,4]-benzothiadiazin-7-ol 5,5-dioxide with 4-(2-methoxy-2-oxoethyl)phenylboronic acid according to the procedure of Example 1, but extending the reaction time to 16 hours. Purification is carried out by chromatography on a silica column, eluting with a mixture of $CH_2Cl_2$/MeOH 98/2.

Melting point: 140-142° C.

Step B: {4-[(5,5-Dioxido-2,3,3a,4-tetrahydro-1H-pyrrolo[2,1-c][1,2,4]benzothiadiazin-7-yl)oxy]phenyl}acetic acid A suspension of the ester obtained in Step A (538 mg, 1.38 mmol) in 6 ml of NaOH solution is stirred at 100° C. for 3 hours 30 minutes. The reaction solution is acidified with 1N HCl and the white precipitate is filtered off to yield the title compound.

Melting point: 166-169° C.

Step C: 2-{4-[(5,5-Dioxido-2,3,3a,4-tetrahydro-1H-pyrrolo[2,1-c][1,2,4]benzothiadiazin-7-yl)oxy]phenyl}-N,N-dimethylacetamide The procedure is as in Step A of Example 3 but replacing the ammonia gas with 2M dimethylamine in THF and 3-{4-[5,5-dioxo-2,3-dihydro-1H-pyrrolo[2,1-c][1,2,4]benzothiadiazin-7-yl)oxy]phenyl}propanoic acid by the compound obtained in Step B. Purification is carried out by chromatography on a silica column, eluting with a mixture of $CH_2Cl_2$/MeOH 99/1, followed by crystallisation from water.

Melting point: 154° C.

Elemental microanalysis:

|  | C | H | N | S |
|---|---|---|---|---|
| theoretical % | 59.83 | 5.77 | 10.47 | 7.99 |
| experimental % | 59.78 | 5.81 | 10.28 | 7.95 |

Step D: (2-{4-[(5,5-Dioxido-2,3,3a,4-tetrahydro-1H-pyrrolo[2,1-c][1,2,4]benzo-thiadiazin-7-yl)oxy]phenyl}ethyl)dimethylamine The procedure is as in Step B of Example 8. Purification is carried out by chromatography on a silica column, eluting with a mixture of $CH_2Cl_2$/MeOH/$NH_4OH$ 97/3/0.3, followed by crystallisation from $Et_2O$.

Melting point: 159° C.

Elemental microanalysis:

|  | C | H | N | S |
|---|---|---|---|---|
| theoretical % | 61.99 | 6.5 | 10.84 | 8.58 |
| experimental % | 62.25 | 6.64 | 10.50 | 8.25 |

EXAMPLE 10

N-(1-{4-[(5,5-Dioxido-2,3,3a,4-tetrahydro-1H-pyrrolo[2,1-c][1,2,4]-benzothiadiazin-7-yl)oxy]phenyl}cyclopropyl)methanesulphonamide Step A: [1-(4-Iodophenyl)cyclopropyl]amine 7.09 ml (24.01 mmol) of Ti(OiPr)$_4$ are added to a solution of 4-iodobenzonitrile (5.0 g, 21.83 mmol) in 140 ml of anhydrous $Et_2O$ and the reaction mixture is cooled to −65° C. To the resulting solution there are then added, dropwise, 16 ml (48.00 mmol) of a 3M solution of magnesium ethyl bromide in $Et_2O$, and the reaction mixture is returned to ambient temperature. Stirring is continued for 1 hour at ambient temperature and 5.53 ml (43.66 mmol) of $BF_3.OEt_2$ are added. Stirring is continued for 1 hour 15 minutes at ambient temperature and 65 ml of 1N HCl are added. A two-phase suspension is obtained; 300 ml of $Et_2O$ and then 200 ml of 1N NaOH solution are added. The suspension is filtered and the filtrate is extracted twice with $Et_2O$. The organic phases are collected, washed (water, saturated NaCl solution), dried over $MgSO_4$ and concentrated by half. The residual solution is extracted with 1N HCl and the expected amine is precipitated as a result of making alkaline with concentrated NaOH solution.

Melting point: 69-72° C.

Elemental microanalysis:

|  | C | H | N | S |
|---|---|---|---|---|
| theoretical % | 41.72 | 3.89 | 5.41 | 48.98 |
| experimental % | 41.79 | 3.96 | 5.35 | 49.35 |

Step B: N-[1-(4-Iodophenyl)cyclopropyl]methanesulphonamide

To a solution of the compound obtained in Step A (3 g, 11.58 mmol) in 50 ml of $CH_2Cl_2$ there are added 2.7 ml (18.05 mmol) of DBU and then, dropwise, a solution of 2.09 g (12 mmol) of methanesulphonic anhydride diluted with 20 ml of $CH_2Cl_2$. The solution is stirred overnight at ambient temperature and then 20 ml of 1N HCl are added. The organic phase is decanted off, washed (saturated NaCl solution) and dried ($MgSO_4$) and, after evaporation in vacuo, the residue is chromatographed over silica ($CH_2Cl_2$/AcOEt 95/5) to yield the title compound.

Melting point: 101-102° C.

Step C: N-{1-[4-(4,4,5,5-Tetramethyl-1,3,2-dioxaborolan-2-yl)phenyl]cyclopropyl}-methanesulphonamide A mixture of 1.75 g (5.19 mmol) of the compound obtained in Step B, 1.71 g (7.27 mmol) of bis(pinacolato)diboron, 1.53 g (15.57 mmol) of AcOK and 127 mg (0.156 mmol) of $PdCl_2$(dppf).$CH_2Cl_2$ in 20 ml of DMSO is stirred for 30 minutes at 85° C. under nitrogen. At ambient temperature, there are added 50 ml of water and the aqueous phase is extracted three times with AcOEt. The organic phases are collected, washed (saturated NaCl solution) and dried ($MgSO_4$). After evaporation in vacuo, the residue is chromatographed over silica ($CH_2Cl_2$/AcOEt 96/4) to yield the title compound.

Elemental microanalysis:

|  | C | H | N | S |
|---|---|---|---|---|
| theoretical % | 56.98 | 7.17 | 4.15 | 9.51 |
| experimental % | 57.11 | 7.20 | 4.19 | 9.70 |

Step D: (4-{1-[(Methylsulphonyl)amino]cyclopropyl}phenyl)boronic acid

A suspension of 810 mg (2.40 mmol) of the compound obtained in Step C and 1.95 g (9.12 mmol) of NaIO$_4$ in a mixture of 25 ml of acetone and 7 ml of 1M aqueous ammonium acetate solution is stirred for 24 hours at ambient temperature. The solid is filtered off and rinsed with copious amounts of acetone. The filtrate is concentrated by half and the residual solution is extracted with AcOEt. The organic phase is washed (saturated NaCl solution) and dried ($MgSO_4$) to yield, after evaporation in vacuo, the title compound.

Step E: N-(1-{4-[(5,5-Dioxido-2,3,3a,4-tetrahydro-1H-pyrrolo[2,1-c][1,2,4]benzothiadiazin-7-yl)oxy]phenyl}cyclopropyl)methanesulphonamide A suspension composed of 290 mg (1.21 mmol) of 2,3,3a,4-tetrahydro-1H-pyrrolo[2,1-c][1,2,4]benzothiadiazin-7-ol 5,5-dioxide, 465 mg (1.82 mmol) of the compound obtained in Step D, 330 mg (1.82 mmol) of copper(II) acetate, 294 μl (3.64 mmol) of pyridine and about 3.5 g of 4 Å molecular sieve in 35 ml of $CH_2Cl_2$ is stirred for 5 hours at ambient temperature. The reaction mixture is filtered and rinsed with $CH_2Cl_2$/MeOH (1/1). The filtrate is concentrated and then directly applied to a silica column, eluting with a mixture of $CH_2Cl_2$/acetone 96/4. The fractions containing the expected compound are collected and evaporated and the residue is taken up in a small amount of ethyl ether. After filtering off the solid, the title compound is collected in the form of a white powder.

Melting point: 192-194° C.

Elemental microanalysis:

|  | C | H | N | S |
|---|---|---|---|---|
| theoretical % | 53.44 | 5.16 | 9.35 | 14.27 |
| experimental % | 53.52 | 5.53 | 9.08 | 14.76 |

PHARMACOLOGICAL STUDY OF COMPOUNDS OF THE INVENTION

Study of the Excitatory Currents Induced by AMPA in *Xenopus oocytes* a—Method:

mRNA's are prepared from cerebral cortex of male Wistar rats by the guanidinium thiocyanate/phenol/chloroform method. The poly ($A^+$) mRNA's are isolated by chromatography on oligo-dT cellulose and injected at a level of 50 ng per oocyte. The oocytes are incubated for 2 to 3 days at 18° C. to permit expression of the receptors and are then stored at 8-10C. Electrophysiological recording is carried out in a Plexiglass® chamber at 20-24° C. in OR2 medium (J. Exp. Zool., 1973, 184, 321-334) by the "voltage-clamp" method using two electrodes, with a third electrode placed in the bath serving as reference.

All the compounds are applied via the incubation medium and the electric current is measured at the end of the application period. AMPA is used in a concentration of 10 μM. For each compound studied, the concentration that doubles (EC2×) or quintuples (EC5×) the intensity of the current induced by AMPA alone (5 to 50 nA) is determined.

b—Results:

The compounds of the invention potentiate the excitatory effects of AMPA to a very considerable degree and their activity is very clearly superior to that of compounds of reference.

By way of example, the compound of Example 1 has an EC2× of 0.1 μM.

PHARMACEUTICAL COMPOSITION

| Formula for the preparation of 1000 tablets each containing 100 mg of N-(2-{4-[(5,5-dioxido-2,3,3a,4-tetrahydro-1H-pyrrolo[2,1-c][1,2,4]benzothiadiazin-7-yl)oxy]phenyl}ethyl)methanesulphonamide (Example 1) | 100 g |
|---|---|
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

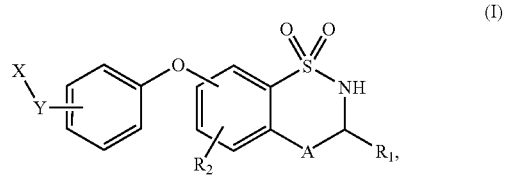

wherein:

$R_1$ represents hydrogen, linear or branched ($C_1$-$C_6$)alkyl or ($C_3$-$C_7$)cycloalkyl, $R_2$ represents hydrogen, halogen or hydroxy, A represents $CR_3R_4$ or $NR_3$ wherein $R_3$ represents hydrogen or linear or branched ($C_1$-$C_6$)alkyl, and $R_4$ represents hydrogen or halogen, or A represents $NR_3$, and $R_1$ and $R_3$, together with the carbon and nitrogen atoms to which they are attached, form a ring

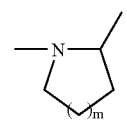

wherein m represents 1, 2 or 3,

Y represents ($C_2$-$C_6$)alkylene optionally substituted by one or more identical or different substituents selected from linear or branched ($C_1$-$C_6$)atkyl and halogen wherein one of the —$CH_2$— groups of the ($C_1$-$C_6$) alkylene moiety may be replaced by a group

wherein p is 1, 2, 3 or 4, or Y represents a group

X represents $NR_5R_6$, $S(O)_nR_7$, $OR_8$, $C(O)R_9$, amidino (optionally substituted by one or two identical or different groups selected from linear or branched ($C_1$-$C_6$) alkyl, hydroxy, linear or branched ($C_1$-$C_6$)alkoxy and

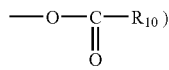

or a heterocyclic group
  wherein
    $R_5$ represents hydrogen, linear or branched ($C_1$-$C_6$) alkyl, $S(O)_tR_{11}$, $C(O)R_{12}$ or $P(O)OR_{13}OR_{14}$,
    $R_6$ represents hydrogen or linear or branched ($C_1$-$C_6$) alkyl, or $R_5$ and $R_6$, together with the nitrogen atom carrying them, form a heterocyclic group,
    $R_8$ represents linear or branched ($C_1$-$C_6$)alkyl or $C(O)R_{15}$,
    $R_9$ represents hydroxy, linear or branched ($C_1$-$C_6$) alkoxy, or amino (optionally substituted by one or two identical or different linear or branched ($C_1$-$C_6$) alkyl),
    $R_7$, $R_{10}$, $R_{11}$, $R_{12}$, $R_{13}$, $R_{14}$ and $R_{15}$, which may be the same or different, each represent hydrogen; linear or branched ($C_1$-$C_6$)alkyl optionally substituted by one or more halogen atoms; aryl-($C_1$-$C_6$)alkyl in which the alkyl moiety is linear or branched; or aryl, n and t, which may be the same or different, each represent 0, 1 or 2,
  its enantiomers and diastereoisomers, and addition salts thereof with a pharmaceutically-acceptable acid or base.

2. A compound of claim 1, wherein A represents $NR_3$, and $R_1$ and $R_3$, together with the carbon and nitrogen atoms to which they are attached, form a ring

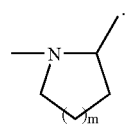

3. A compound of claim 1, wherein $R_2$ represents hydrogen.

4. A compound of claim 1, wherein Y represents an alkylene chain having 2 or 3 carbon atoms.

5. A compound of claim 1, wherein X represents $NR_5R_6$ or $C(O)R_9$.

6. A compound of claim 1, which is N-(2-{4-[(5,5-dioxido-2,3,3a,4-tetrahydro-1H-pyrrolo[2,1-c][1,2,4]benzothiadiazin-7-yl)oxy]phenyl}ethyl) methanesulphonamide, its enantiomers and diastereoisomers, and addition salts thereof with a pharmaceutically-acceptable acid or base.

7. A pharmaceutical composition comprising as active principle an effective amount of a compound of claim 1, together with one or more pharmaceutically-acceptable excipients or vehicles.

8. A method for treating a living animal body, including a human, afflicted with a condition selected from anxiety and depression, comprising the step of administering to the living animal body, including a human, an amount of a compound of claim 1, which is effective for alleviation of the condition.

* * * * *